US012782336B2

(12) United States Patent
Laugharn, Jr. et al.

(10) Patent No.: US 12,782,336 B2
(45) Date of Patent: Nov. 3, 2026

(54) PROTEIN AND METABOLITE ENRICHMENT USING FOCUSED ACOUSTIC ENERGY

(71) Applicant: Covaris, LLC, Woburn, MA (US)

(72) Inventors: James A. Laugharn, Jr., Boston, MA (US); Ulrich Thomann, Stow, MA (US); Nicolas Alexandre Julien Autret, Torcy (FR); Eugenio Daviso, Pelham, NH (US); Hamiduddin Khoja, Rancho Santa Margarita, CA (US)

(73) Assignee: Covaris, LLC, Woburn, MA (US)

( * ) Notice: Subject to any disclaimer, the term of this patent is extended or adjusted under 35 U.S.C. 154(b) by 1134 days.

(21) Appl. No.: 17/699,330

(22) Filed: Mar. 21, 2022

(65) Prior Publication Data

US 2022/0299498 A1 Sep. 22, 2022

Related U.S. Application Data

(60) Provisional application No. 63/163,302, filed on Mar. 19, 2021.

(51) Int. Cl.

| | |
|---|---|
| ***G01N 33/49*** | (2006.01) |
| ***B01D 61/14*** | (2006.01) |
| ***C07K 1/36*** | (2006.01) |
| ***C07K 14/765*** | (2006.01) |
| ***C07K 14/81*** | (2006.01) |

(52) U.S. Cl.

CPC ......... *G01N 33/491* (2013.01); *B01D 61/145* (2013.01); *C07K 1/36* (2013.01); *C07K 14/765* (2013.01); *C07K 14/8125* (2013.01)

(58) Field of Classification Search

CPC ........ B01D 61/145; C07K 1/14; C07K 1/145; C07K 1/36; C07K 14/765; C07K 14/8125; G01N 33/491; G01N 33/6803

See application file for complete search history.

(56) References Cited

U.S. PATENT DOCUMENTS

2017/0283788 A1* 10/2017 Khoja .................... C12N 13/00
2020/0166520 A1* 5/2020 Tan .................... G01N 33/6848

OTHER PUBLICATIONS

International Preliminary Report on Patentability for International Application No. PCT/US2022/020516, mailed Sep. 28, 2023.
PCT/US2022/020516, Jun. 23, 2022, International Search Report and Written Opinion.
International Search Report and Written Opinion for International Application No. PCT/US2022/020516, mailed Jun. 23, 2022.

(Continued)

*Primary Examiner* — Dirk R Bass
(74) *Attorney, Agent, or Firm* — Wolf, Greenfield & Sacks, P.C.

(57) ABSTRACT

Apparatus and method for disassociating protein complexes, e.g., to allow recovery and/or analysis of at least one of the proteins or metabolites released from a complex. Disassociation is done using focused acoustic energy and without solvents, excessive heat or other process conditions that damage proteins or metabolites. Disassociation may be followed by depletion of one of the proteins released from complexes, e.g., to allow another protein or metabolite released from the complexes to be recovered.

27 Claims, 7 Drawing Sheets

(56) References Cited

OTHER PUBLICATIONS

Dragusanu et al., On-line bioaffinity-electrospray mass spectrometry for simultaneous detection, identification, and quantification of protein-ligand interactions. Journal of the American Society for Mass Spectrometry. Oct. 1, 2010;21(10):1643-8.

Echan et al., Depletion of multiple high-abundance proteins improves protein profiling capacities of human serum and plasma. Proteomics. Aug. 2005;5(13):3292-303.

* cited by examiner

PROTEIN AND METABOLITE ENRICHMENT USING FOCUSED ACOUSTIC ENERGY

CROSS REFERENCE TO RELATED APPLICATION

This application claims the benefit of U.S. Provisional Application No. 63/163,302, filed Mar. 19, 2021, which is hereby incorporated by reference in its entirety.

BACKGROUND

1. Field of Invention

Methods and apparatus for enrichment of proteins and/or metabolites, e.g., to enable downstream analysis of targeted proteins, metabolites and/or peptides by liquid chromatography coupled to mass spectrometry or other techniques.

2. Related Art

Plasma is the soluble component of human blood which harbors thousands of proteins originating from a variety of cells and tissues through either active secretion or leakage from blood cells or tissues. A wide variety of proteins and protein isoforms (100 or more) are found in biological fluids, such as blood plasma. Some of these proteins are found in relatively high concentrations, also called as high abundant proteins (e.g., albumin, IgG, antitrypsin, IgA, transferrin, haptoglobin, fibrinogen). However, other proteins, which are of interest as biomarkers for monitoring critical disease states are found in significantly lower concentrations. The difference in concentration can result in the more abundant proteins interfering with recovery and analysis of less abundant proteins. To enable easier, accurate identification and quantitation of specific less abundant proteins, the more abundant proteins can be removed from the sample using one or more known processes. The process of protein removal, also known as depletion can enable easy identification, quantitation and analysis of less abundant proteins. Ensuring even distribution of such less abundant proteins is a key pre-analytical prerequisite, including in recovery approaches which do not include a depletion strategy.

Metabolites are critical for controlling several cellular functions and are directly involved in the processes essential for normal cell development and reproduction. The types of metabolites comprise an extensive list ranging from amino acids, carboxylic acids, alcohols, antioxidants, nucleotides, polyols or even vitamins. Studying metabolites provides comprehensive information about cellular activity. Metabolites are known to interact with proteins, especially in a non-specific manner, resulting in their impaired recovery.

SUMMARY OF INVENTION

The inventors have appreciated that sampling techniques for protein depletion can benefit from prior release of metabolites in the preparation medium, and that typical depletion processes, such as precipitation and immunoaffinity, can undesirably remove proteins of interest from a sample along with removal of more abundant proteins. For example, a sample may include a first protein that occurs in relatively low concentration, and another second protein in high concentration. The second protein may have a concentration that is one or more orders of magnitude higher than the first protein. In some cases, the first and second proteins may be bound together to form a complex, e.g., in which the first protein is sequestered or chaperoned by the second protein. As an example, amyloid-β peptides, a known marker for Alzheimer's disease, bind rapidly to human serum albumin (HSA), complicating its accurate identification and quantitation by immunoassays. The proteins in the complexes are typically bound to each other via weak bonds (e.g. ionic, hydrogen, etc.). These protein complexes typically are bound via weaker bonds (e.g., ionic, hydrogen, etc.) compared to covalent bonds. However, the first protein may be captured and sequestered in the hydrophobic core of the second protein resulting in both proteins moving together. Thus, if the second protein is depleted from the sample in an effort to enrich the first protein, any first protein that is complexed with the second protein will be removed as well. Therefore, analytical assays for identification and/or quantitation of the first protein might be erroneous. Furthermore, low-abundance proteins can also be sequestered in membrane-bound vesicles such as exosomes and can be used as biomarkers for several diseases, such as, cancer. Depletion methodologies can also lead to loss of these low abundance proteins sequestered in exosomes.

In some embodiments, systems and methods are provided for disassociating proteins and/or metabolites from complexes, thereby ensuring low abundance proteins or metabolites can be recovered at a higher rate, identified, quantified, and/or analyzed. In some cases, the individual high abundance proteins can be more efficiently depleted by disassociating them from lower abundance proteins/metabolites using focused acoustic energy and without employing typical techniques and/or materials, such as techniques that employ solvents effective to perform the disassociation itself, excessive heat, affinity processes, etc. Use of focused acoustic energy-based separation can ensure that disassociation of protein complexes is performed without damaging the targeted proteins and/or other materials in the sample. In some cases, disassociation and enrichment of proteins can be performed with the sample including complexes in a non-denaturing buffer, which in turn can ensure easier downstream processing. The released proteins can then be subjected to processing and analysis, such as depletion, LC-MS analysis, or ELISA-based assay. Biomolecules recovered from cells can be subjected to any analytical process for efficient identification and quantitation. Similarly, metabolites can be disassociated from proteins using focused acoustic energy without excessive heat, and thus, without risking their stability. The released metabolites can be subjected to structural and quantitative analytical processes, such as, LC-MS or NMR spectroscopy. Focused acoustic energy-based sample preparation method ensures reliable and reproducible protein and metabolite analysis results from samples.

In some embodiments, a sample with a mixture of different proteins is provided with at least two of the types of proteins forming complexes in which a first protein is bound to a second protein. Focused acoustic energy can be employed to disrupt the plurality of complexes, disassociating the first protein from the second protein. In some cases, the disassociation of the first and second proteins can be achieved without use of any solvent that is typically used for chemical separation of the proteins involved in complex followed by dissolution of both proteins. In some embodiments, a method of analyzing proteins and/or metabolites in a sample is provided including at least one protein and a metabolite, in which the metabolite is bound to the protein to form a plurality of complexes. Focused acoustic energy can disrupt the plurality of complexes and disassociate the metabolite from the protein of each of the complexes. In some cases, the disassociation of the metabolite and protein can be achieved without use of a solvent. In some cases, focused acoustic energy can disassociate both protein/protein and protein/metabolite complexes at the same time and/or in the same sample.

In some cases, the second protein can be of a higher molecular weight than the first protein, or the protein that forms a complex with the metabolite can have higher molecular weight than the metabolite. As an example, the first protein may be sequestered at least partially within the second protein, and/or the metabolite may be sequestered at least partially within the protein with which it forms a complex. Post-disassociation of the first protein and/or metabolite from the complex-forming protein, the complex-forming protein may be depleted in the sample. In some cases, the sample includes blood plasma, and the concentration of the first protein present in the sample is at least an order of magnitude lower than the concentration of the second protein. Similarly, the sample may include blood plasma, and the concentration of the metabolite can be at least an order of magnitude lower than the concentration of the protein with which the metabolite forms a complex. Of course, the first protein and/or the metabolite may be present in the sample free of any complex with a protein/proteins or metabolites other than the first and second types of proteins or metabolite. Some of the types of complexes that may be disassociated include HSA-Ibuprofen, HSA-fatty acids, HAS-propofol, HSA-Thyroxine, HSA-heme-Fe(III), and HSA-bilirubin. Disassociation of the first and second proteins or metabolite and protein from the complexes may increase measurable concentration of the first protein or metabolite in the sample. In some cases, the disassociation of the first and second proteins or of the metabolite and protein can be achieved without use of a solvent effective to perform the disassociation.

In some embodiments, a sample is exposed to focused acoustic energy while the sample includes a protein depletion medium, such as magnetic beads, configured to bind to proteins targeted for depletion from the sample. In some cases, acoustic energy can cause disassociation of complexes as well as enhance binding of targeted proteins with the depletion medium. In some embodiments, the proteins targeted for depletion can include albumin and immunoglobulin. In some embodiments, a protein or metabolite to be recovered, identified or otherwise analyzed after disassociation form a complex that includes Alpha-1-acid glycoprotein, synaptotagmin-13 and Heparin cofactor-2.

In some embodiments, a total amount of focused acoustic energy applied to the sample and/or other acoustic energy parameters such as peak incident power, duty cycle, cycles per burst, etc., can be adjusted to a level for optimal disassociation of selected ones of the plurality of complexes and/or to adjust a level or rate at which the first protein or metabolite is disassociated from complexes. For example, certain proteins may be more effectively disassociated from complexes for a given total amount of focused acoustic energy and/or energy having certain parameters, whereas other proteins may be more effectively disassociated from complexes using different focused acoustic energy arrangements. Focused acoustic energy parameters, such as average total incident energy, can be adjusted according to the size, nature (such as, hydrophobicity) of protein(s) or metabolite(s) are of interest for recovery, identification or quantitation in a sample.

Other advantages and novel features of the invention will become apparent from the following detailed description of various non-limiting embodiments when considered in conjunction with the accompanying figures and claims.

BRIEF DESCRIPTION OF THE DRAWINGS

Aspects of the invention are described with reference to the following drawings in which numerals reference like elements, and wherein.

DETAILED DESCRIPTION

Figure 1:
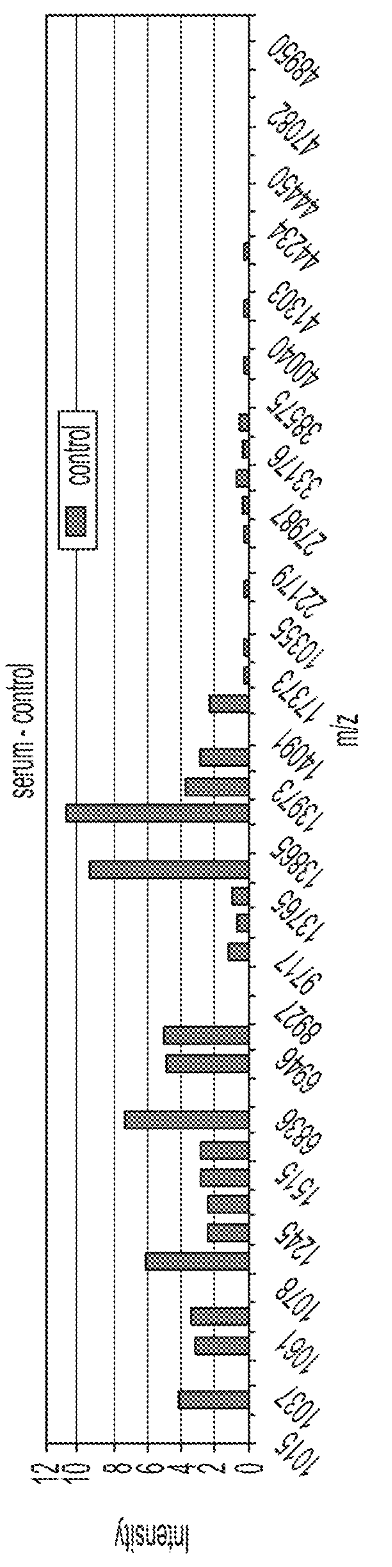
FIG. 1 shows mass spectrometry results of a blood serum sample that was not exposed to focused acoustic energy to disassociate protein complexes.

Aspects of the present disclosure are not limited in application to the details of construction and the arrangement of components set forth in the following description or illustrated in the drawings. Other embodiments may be employed and aspects of the present disclosure may be executed in various ways. Also, the phraseology and terminology used herein is for the purpose of description and should not be regarded as limiting.

As described above, samples containing protein/protein complexes and/or metabolite/protein complexes may be disassociated by exposing samples to focused acoustic energy. Disassociation may free proteins and/or metabolites from a corresponding complex-forming protein, thereby allowing for the recovery, analysis or other processing of the freed proteins and/or metabolites. Disassociation may be done without the use of solvents, relatively high temperatures (e.g., over 50 degrees C.), or other process conditions that can damage the proteins or metabolites.

Figure 2:
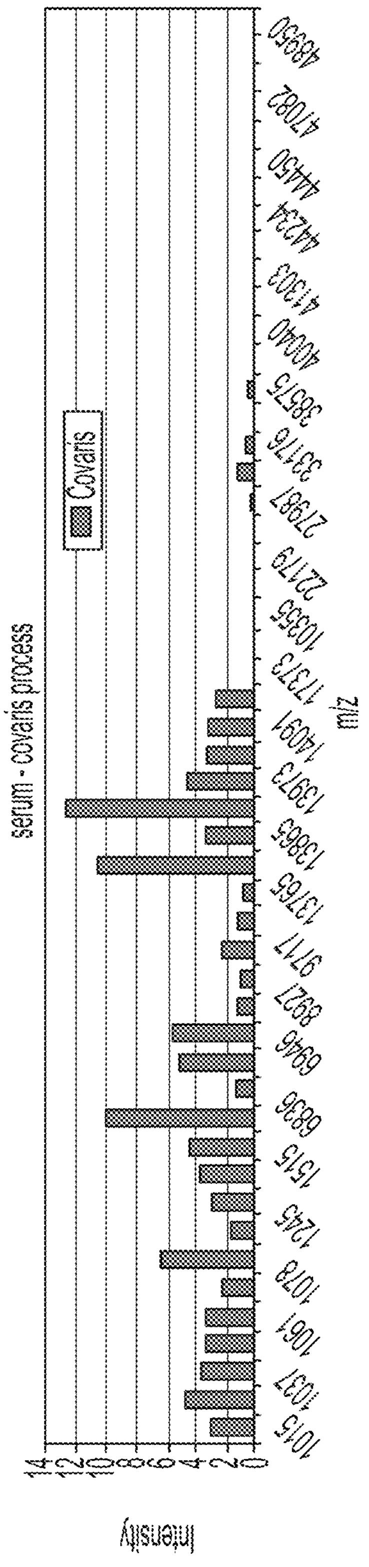
FIG. 2 shows mass spectrometry results of a blood serum sample that was exposed to focused acoustic energy to disassociate protein complexes.

FIGS. 1 and 2 show LC-MS results from an experiment that illustrates the potential benefits of using focused acoustic energy to disassociate protein/protein complexes and/or metabolite/protein complexes in accordance with some embodiments. In this experiment, 5 microliter serum samples were recovered from a blood sample and each was diluted with 20 microliters of buffer (PBS, Phosphate-buffered saline). A control sample, which was not subjected to treatment with focused acoustic energy, was subjected to mass spectrometry analysis using a Bio-Rad ProteinChip system (Bio-Rad, Pleasanton CA) and the results are shown in FIG. 1. FIG. 1 shows that 33 peaks were identified, representing 33 different proteins in the sample. Another portion of the sample was subjected to focused acoustic energy followed by LC-MS analysis. Regarding focused acoustic energy treatment, the sample was subjected to focused acoustic energy for 5 seconds using a Covaris S2 system (Covaris, Inc., Woburn MA). Acoustic energy treatment parameters were 200 W peak incident power (PIP), 20% duty cycle and 100 cycles per burst, with a water coupling medium at a temperature of 5 degrees C. The results of analysis of the focused acoustic energy-treated sample are shown in FIG. 2, which shows 44 peaks or protein compounds identified in the sample. Compared to the untreated sample, the sample treated with focused acoustic energy exhibited larger number of protein compounds, in particular, larger number of lower molecular weight proteins. This can be seen on the left side of FIGS. 1 and 2; FIG. 2 shows compounds at around m/z of 1015, 1045, 1079, 6800 and 8940, whereas the FIG. 1 results show none. It is believed these additional compounds identified in FIG. 2 resulted from proteins being disassociated from protein/protein complexes. From this experiment, the inventors have concluded that focused acoustic energy can be used to successfully disassociate proteins from protein/protein complexes as well as metabolites from metabolite/protein complexes in other applications. Below are several example applications for focused acoustic energy to disassociate the analytes from complexes.

Example One: ELISA

In this example, the effects of focused acoustic energy in separating Amyloid-Beta from human serum albumin (HSA) is explored. Amyloid-Beta in a person's blood is a biomarker for determining whether the person is at risk of having Alzheimer's disease. The process is as follows:

1. Procure Amyloid-Beta peptides, Human Serum Albumin (HSA), Albumin depletion columns, and an Amyloid-Beta ELISA kit. Alternatively, human plasma could be used in place of HSA.
2. Mix and incubate a suitable concentration of the Amyloid-Beta peptides in HSA for 1 hour at 25 degrees C.
3. Treat the samples with focused acoustic energy for disassociation of protein complexes; other samples are not treated and are control samples.
4. Use an Albumin depletion column to remove the HSA and Amyloid-Beta/HSA complexes.
5. Treat the eluate with focused acoustic energy to homogenize the samples.
6. Carry out an ELISA for Amyloid-Beta.
7. Calculate data for amount of Amyloid-Beta detected for focused acoustic energy treated samples, as well as samples not subjected to focused acoustic energy.
8. Calculate reproducibility and Z'.

The focused acoustic energy treated samples are expected to have a greater amount of Amyloid-Beta than the control samples. Also, an improved % CV and an improved Z1 with focused acoustic energy treated samples should be found as compared to the control samples.

Example Two: Mass Spectrometer-Based Analysis/Proteins

In this experiment, the effects of focused acoustic energy in protein dissociation are illustrated using a bottom-up proteomic approach.

1. Procure Amyloid-Beta peptides, and Albumin depletion columns.
2. Procure good quality, fresh human plasma preferably from a mix of young donors.
3. Follow a suitable protocol for mixing and incubating the prescribed concentration of the Amyloid-Beta peptides in HSA for 1 hour at 25 degrees C.
4. Treat some of the samples with focused acoustic energy for disassociation of complexes; other samples are not treated and are control samples.
5. Use an Albumin depletion column to remove the HSA and Amyloid-beta/HSA complexes.
6. Provide aliquots of the samples for bottom up proteomics analysis.
7. Analyze for plasma proteins identified.
8. Analyze for abundance of the Amyloid-Beta as compared to HSA.

The focused acoustic energy treated samples are expected to have a greater number of plasma proteins identified. The focused acoustic energy treated samples should also have a greater percentage of Amyloid-Beta peptides identified as compared to the background HSA peptides.

Example Three: Mass Spectrometer Based Analysis/Metabolites

In this experiment, the effects of focused acoustic energy in protein/metabolites dissociation are illustrated using a mass spectrometry approach.

1. Employ a sample preparation method such as that in Dunn et al (doi:10.1038/nprot.2011.335, PMID 21720319).
2. Procure good quality fresh human plasma preferably from a mix of young donors.
3. Aliquot 125 ul of plasma in 500 ul tube and add 375 ul of methanol.
4. Treat the samples with focused acoustic energy and pellet the protein precipitate; other samples are not treated with focused acoustic energy and are control samples.
5. Transfer the supernatant into a microcentrifuge tube and dry down.
6. Analyze for plasma metabolites identified against untreated samples.

The focused acoustic energy treated samples are expected to have a greater number/greater diversity of plasma metabolites identified. The focused acoustic energy treated samples should also show greater data consistency and reproducibility.

Example Four: Affinity-Depletion of High Abundance Plasma Proteins

The dynamic range of protein concentration in blood plasma ranges across 10 orders of magnitude. For example, important biomarkers such as cytokines, insulin, c-reactive protein are present in picogram per milliliter levels, whereas albumin, globulins (IgA, IgM, IgG, macroglobulin, transferrin, etc.) are in the milligrams per milliliter level. This wide range of concentration represents a major challenge for protein analysis—from proteomics to biomarker diagnostics—since a few high abundance protein species represent over 80% of the total protein content. For analytical technologies, such as, LC-MS or ELISA, the wide range in stochiometric ratios may reduce the detection limit of low abundance proteins and peptides owing to an overload of signal from the abundant proteins.

Removal of high abundance proteins before downstream analysis, especially for targeted or bottom-up analysis can be one method to circumvent the signal overload issue, however, it has its own risks. Multiple suppliers offer 'depletion' kits that are either affinity-based or use chemical precipitation processes. However, such depletion kits or other high abundance protein depletion protocols can also impact the outcome by removing low abundance proteins of interest along with high abundance proteins. One example is the removal of low abundance proteins, peptides and even metabolites due to absorption/binding of these low abundance proteins to the high abundance proteins, especially albumin. When the high abundance proteins are removed, depleted or otherwise separated from other parts of the sample, the bound or absorbed proteins/metabolites can be removed along with the high abundance proteins. One example is the reduction and variability across blood plasma samples in cytokine detection after using albumin depletion kits such as the Montage Albumin Deplete Kit (Millipore-Sigma) (Granger et al. 2005|DOI:10.1002/pmic.200401331). In order to avoid or minimize simultaneous removal of biomarkers (proteins and/or metabolites) during high abundance plasma protein depletion, the plasma sample is diluted with a buffer (1:100 vol/vol) before adding depletion resin to reduce the dissociation constant of the protein complexes, facilitate dissociation of biomarkers from albumin, etc. However, this approach can have disadvantages such as substantially increasing the sample volume and processing time.

The inventors have discovered that dissociation of protein complexes can be efficiently achieved by application of focused acoustic energy, and in some cases without overly excessive dilution of samples. An experiment to prove this involved PureProteome Human Albumin and Immunoglobulin Magnetic Beads kit (EMD Millipore Cat # LSK-MAGHDKIT) (hereafter PureProteome kit) was used as a comparison/control, and when used as instructed by the manufacturer, enables high depletion efficiency of Albumin and most Immunoglobulins from human serum or plasma samples. However, other resin-based immune-depletion kits for high abundance plasma proteins can be substituted for the PureProteome kit.

One of many examples is the Proteome Purify 12 Kit (R&D Systems Cat # IDR012-020) which is described to bind and deplete a larger range of protein, such as α1-Acid Glycoprotein, α1-Antitrypsin, α2-Macroglobulin, Albumin, Apolipoprotein A-I, Apolipoprotein A-II, Fibrinogen, Haptoglobin, IgA, IgG, IgM, Transferrin.

For comparison samples, raw human blood plasma was treated using the PureProteome Kit per the manufacturer's protocol. 25 microliter samples of human plasma were diluted to 100 microliters with 1×PBS. 900 microliters of PureProteome magnetic beads were washed with 1×PBS before mixing with the diluted plasma samples. The samples were then mixed on a turntable for 1 hour at room temperature before matrix with bound (depletion targeted) proteins was collected by centrifugation (5 minutes at 5,000×g) and the supernatant removed. Magnetic beads were washed 3 times with 500 microliters 1×PBS by vortexing for 10 seconds. Supernatants were collected as previously described and combined with the depleted plasma. The final volume was 1.6 mL which is a dilution factor of 64 and is recommended to facilitate out-dilution/dissociation of protein complexes to avoid co-depletion of non-targeted proteins. ("Non-targeted" meaning proteins that are not targeted for depletion or separation from other sample portions. The non-targeted proteins for purposes of depletion may in fact be targeted for later identification, recovery, analysis, etc.) The supernatant was then concentrated via the included Amicon Ultra-2 3k Centrifugal Filter Device to about 100 microliters.

To form samples to assess the effectiveness of focused acoustic energy in enhancing recovery of low abundance proteins and other materials not targeted by the depletion process, raw human blood plasma was treated using the PureProteome Kit with a modified protocol that includes the use of focused acoustic energy treatment. 36 microliters of PureProteome magnetic beads were washed with 1×PBS before mixing with 2 microliters of undiluted human plasma. Samples were treated with focused acoustic energy in scanning mode for up to 2 hours to facilitate disassociation of protein complexes and depletion of disassociated albumin and immunoglobulins. Specifically, samples were provided in a 96 AFA-TUBE TPX Plate (Covaris, 520291) with PS Rack 96 AFA-TUBE TPX Plate (Covaris, 500622) in a Covaris LE220-plus Focused-ultrasonicator (Covaris, 500569). Samples were treated with 500 W PIP (peak incident power), 25% DF (duty factor or duty cycle), 1000 CpB (cycles per burst), at a scanning rate of 10 mm/sec in a 12 degree Celsius water bath for 35 to 500 iterations. Following focused acoustic energy treatment, matrix with bound (depletion targeted) proteins was collected by centrifugation (5 minutes at 5,000×g) and the supernatant transferred into a DNA LoBind Microcentrifuge Tube (Eppendorf, 022431021).

The protein content of all samples was quantified using the Pierce™ BCA Protein Assay Kit (Thermo Scientific, 23225) per manufacturer's protocol. 25 microliter samples were pipetted into a Corning™ UV-Transparent Microplate (Thermo Scientific, 3635) before adding 200 microliters BCA working reagent. Following a 30 minute incubation at 37 degrees Celsius, absorbance was measured at 562 nm on a plate reader. Protein concentrations were calculated from a standard curve. All samples were diluted to 0.7 mg/mL using 1×PBS.

Following normalization of protein concentrations, all samples were analyzed with SDS-PAGE. 5 microliters of depleted plasma (containing 3.35 micrograms protein) was mixed with 4.75 microliters 2× Laemmli Sample Buffer (Bio-Rad, 1610737) and 0.25 microliters β-mercaptoethanol before heating at 95 degrees Celsius for 5 minutes. Prepared samples were loaded onto a 4-20% Criterion™ TGX Stain-Free™ Protein Gel (Bio-Rad, 5678093) and run at a constant 200 V for 40 minutes in a Criterion™ Vertical Electrophoresis Cell with a PowerPac Basic Power Supply (Bio-Rad, 1656019). The gel was imaged using a Gel Doc™ EZ System (Bio-Rad, 1708270EDU).

The differences in the workflows employed in this example are summarized in Table 1. The workflow with focused acoustic energy (Modified Protocol—Focused Acoustics enhanced) is readily amenable to automation for high throughput assays because of the workflow's compatibility with 96-well plates, thereby reducing amount of plasma input while eliminating the post-treatment concentration step (Ultrafiltration). In contrast, workflows for depletion of high abundance protein in plasma including the PureProteome kit (Manufacturer Protocol) are not automatable, because the relatively high sample volume precludes the ability to use 96-well plates, and hence cannot be used for high throughput assays in plasma proteomics.

TABLE 1

| | Manufacturer Protocol | Modified Protocol - Focused Acoustics enhanced |
|---|---|---|
| Incubation Time (min) | 60 | Depends on # of scans (15 to 120 min) |
| Mixing Method | Turntable | LE220-plus |
| Tube Format | Single Tube | 96 AFA-TUBE TPX Plate |
| Dilution during Binding | 1:64 | 1:25 |
| Plasma Volume (uL) | 25 | 2 |
| PureProteome Matrix Volume (uL) | 1575 | 48 |
| Total Volume (uL) | 1600 | 50 |
| Eluate compatible with direct Trypsin Digest | No | Yes |
| Automatable | No | Yes |
| Concentration step | 60 min | N/A |
| Binding Buffer | PBS | PBS |
| Depletion Medium | PureProteome Albumin/Immunoglobulin Magnetic beads | PureProteome Albumin/Immunoglobulin Magnetic beads |

Figure 3:
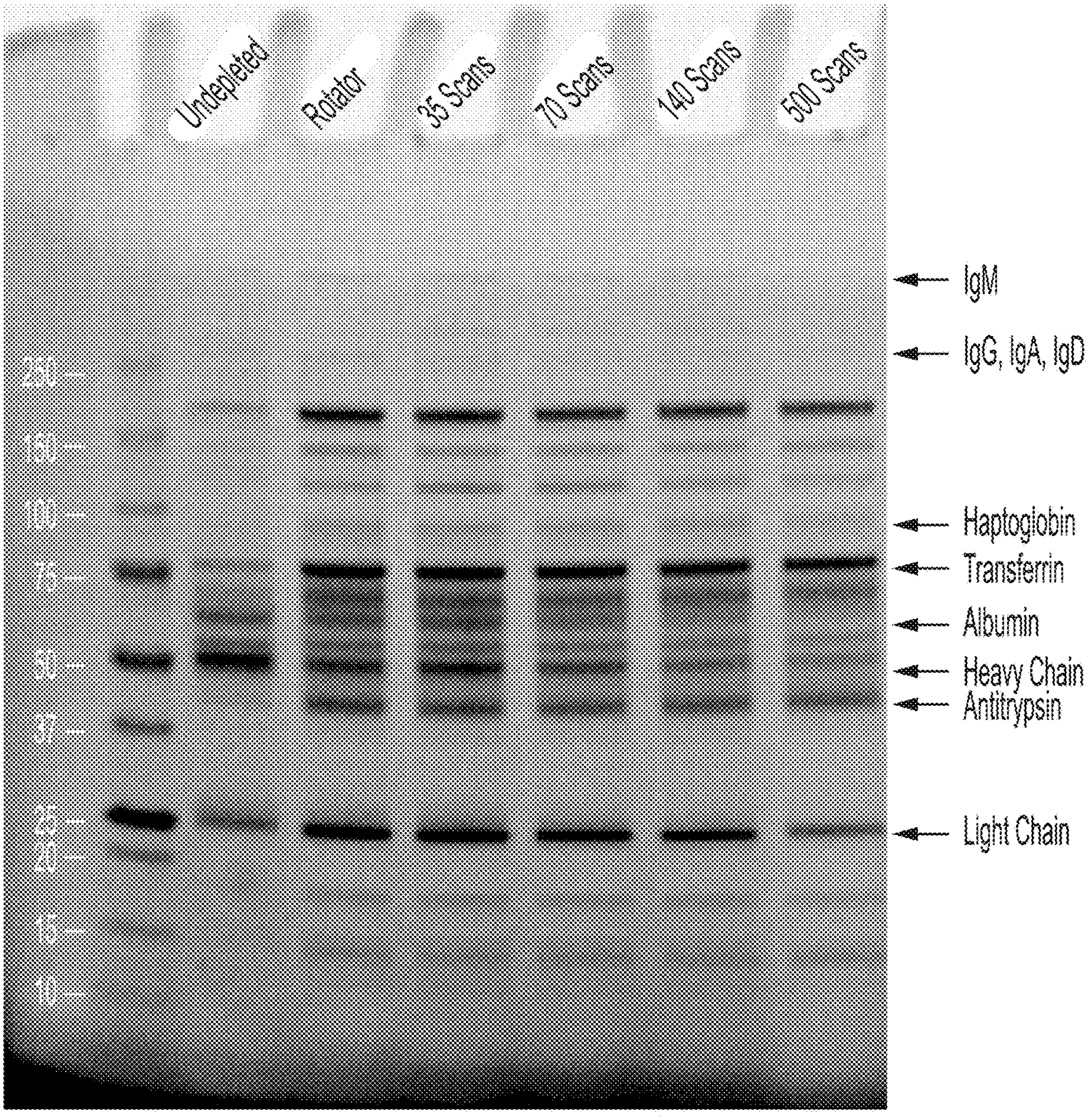
FIG. 3 shows SDS-PAGE analysis of multiple blood plasma samples that are untreated, processed using a commercial depletion kit according to manufacturer instructions, and processed using a modified protocol of the commercial depletion kit employing focused acoustic treatment.

Samples were normalized to the same concentration (0.7 micrograms/microliter) and analyzed by SDS-PAGE. Results of the SDS-PAGE analysis are shown in FIG. 3. In FIG. 3, the Undepleted represents protein analysis results for raw plasma; Rotator indicates depleted plasma samples processed according to the PureProteome kit (Manufacturer Protocol) without acoustic energy; and 35 Scans, 70 Scans, 140 Scans, 500 Scans indicate plasma treated using the modified protocol for the PureProteome kit with focused acoustic energy using the corresponding number of scans per sample. As can be seen in FIG. 3, several proteins were detected from samples that were run with focused acoustics, which were obscured by high abundance proteins (such as albumin) in assays without focused acoustics.

Figure 4:
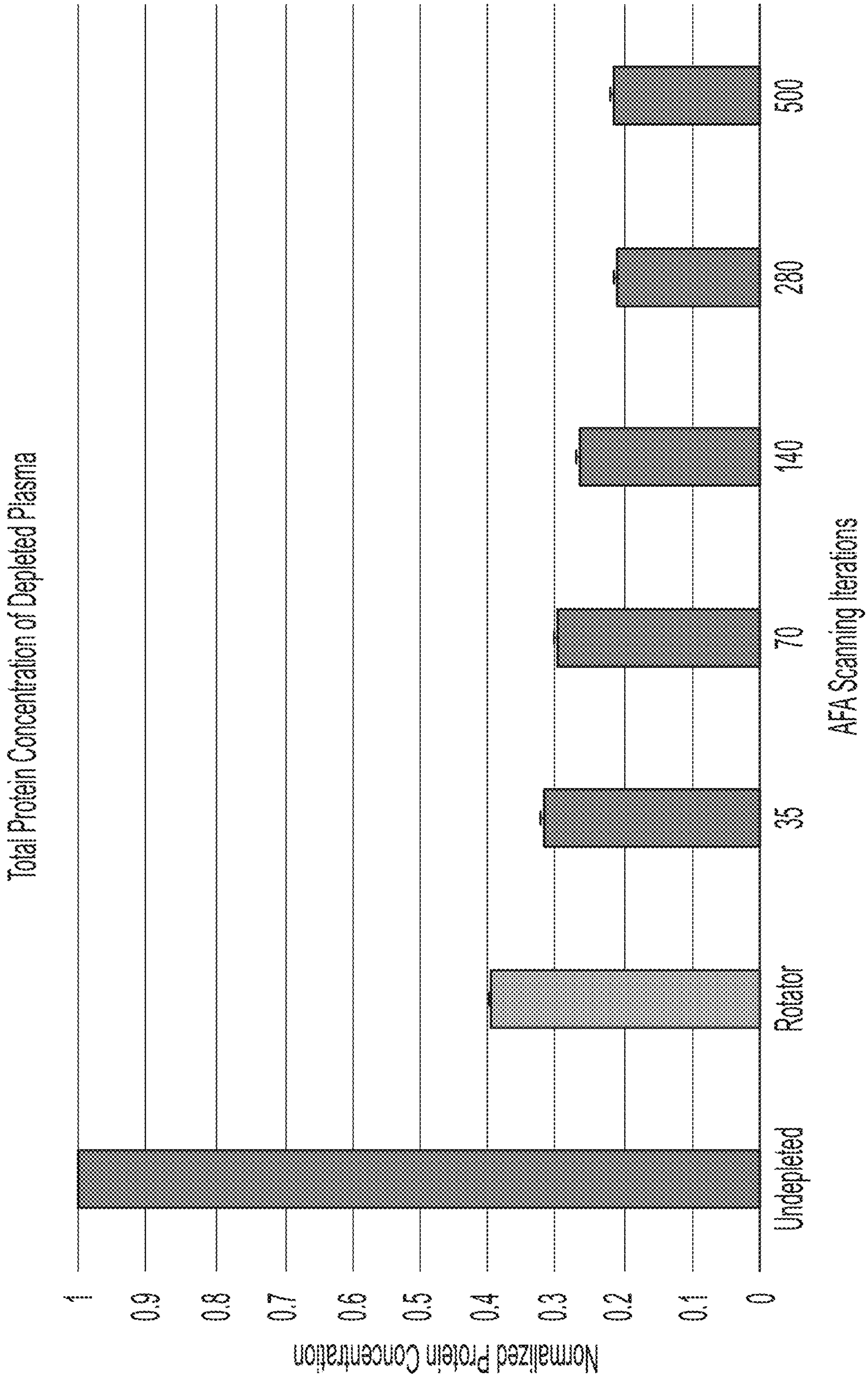
FIG. 4 shows total protein concentration in the samples of FIG. 3.

Depletion efficiency of the targeted high-abundance proteins can also be measured simply as total protein concentration in the supernatant before and after exposure to the PureProteome depletion medium. For example, FIG. 4 shows total protein concentration for samples processed as in the examples of FIG. 3. As demonstrated in this experiment, treatment of raw plasma with the depletion medium removes about 75-85% of protein, which is in good agreement with the reported amounts of albumin and immunoglobulins in normal human blood plasma. As expected, the depletion of albumin/immunoglobulin is more efficient if focused acoustic energy is applied during the binding process. This use of focused acoustic energy also enriches non-targeted proteins (biomarkers), as discussed below.

In order to compare which proteins were depleted versus those being enriched in the raw and depletion medium-treated plasma samples, all seven sample types from FIGS. 3 and 4 were subjected to tryptic digest, following separation and analysis via LC-MS. In short, a total of 10 micrograms of protein in each of the plasma samples normalized to 0.7 micrograms/microliter protein concentration were analyzed by LC-MS. Since the samples are in PBS buffer, they could be directly used in trypsin-digests, followed by labeling of peptides with stable isotope (TMT10). All seven sample types were then pooled for LC-MS analysis. A list of identified proteins based on database hit frequency were obtained from this analysis.

Data analysis revealed that the targeted proteins (those expected to be removed by the PureProteome depletion medium) are indeed depleted in the treated plasma fractions as compared to raw plasma. Table 2 shows the relative abundance of albumin and selected immunoglobulins (IgG and Ig lambda) in raw and depletion medium-treated plasma. The Depletion Factor is defined as the ratio of the combined albumin and immunoglobulin abundance in raw plasma to depletion medium-treated plasma. Thus, the enrichment of non-targeted plasma proteins should theoretically be approximately 5.4 fold in the PureProteome kit (Manufacturer protocol) treated sample, and 2.4, 2.8, 3.9, 3.7 and 4.9 fold in each of the focused acoustic energy treated (i.e., AFA35, AFA70. AFA140, AFA280 and AFA500 scans) samples as shown in Table 2.

TABLE 2

| Targeted Protein | Raw Plasma | PureProteome | AFA 35 | AFA 70 | AFA 140 | AFA 280 | AFA 500 |
|---|---|---|---|---|---|---|---|
| | Number of Hits (LC-MS) | | | | | | |
| Albumin | 70050 | 11524 | 21884 | 16808 | 16429 | 18188 | 14292 |
| IgG | 16063 | 4029 | 12152 | 12152 | 5180 | 4344 | 3129 |
| Ig lambda | 2318 | 937 | 2958 | 2958 | 1210 | 1072 | 809 |
| total | 88431 | 16490 | 36994 | 31918 | 22819 | 23604 | 18230 |
| Depletion Factor relative to Raw | Albumin | 6.1 | 3.2 | 4.2 | 4.3 | 3.9 | 4.9 |
| | IgG | 4.0 | 1.3 | 1.3 | 3.1 | 3.7 | 5.1 |
| | Ig lambda | 2.5 | 0.8 | 0.8 | 1.9 | 2.2 | 2.9 |
| | Total | 5.4 | 2.4 | 2.8 | 3.9 | 3.7 | 4.9 |

However, as expected, the enrichment of non-targeted proteins in a passively mixed PureProteome depletion medium-treated plasma does not follow this theoretical ratio. Table 3 lists selected number of proteins and their actual enrichment after depletion medium treatment with and without focused acoustic energy. The results indicate that enrichment of non-targeted (e.g., low-abundance and/or complexed) proteins significantly enhanced in presence of focused acoustic energy. This is believed to be due to the nano and micro-mixing effects induced by focused acoustic energy, enabling dissociation of low abundant proteins from 'carrier' proteins such as albumin and immunoglobulins that are targeted for depletion. In absence of such nano-mixing forces, proteins that are bound to the targeted high abundance proteins are co-depleted. Thus, although a 5.4 fold enrichment of non-targeted proteins in the PureProteome kit (Manufacturers protocol) should be expected, the actual enrichment of selected biomarkers (non-targeted proteins for depletion) is slightly above factor of 1.1. In contrast, in presence of focused acoustic energy, the enrichment was found to be up to about 10 fold for certain biomarkers, significantly higher than the theoretically calculated values based on albumin/immunoglobulin de-complexing and depletion. These results clearly demonstrate that sequestered proteins of interest contribute to co-depletion with high abundance proteins. There is no advantage to use depletion media if sequestered and complexed proteins cannot be dissociated from high abundance carrier proteins. Focused acoustic energy allows for this dissociation and subsequent recovery, followed by identification and/or quantitation of low abundant proteins.

biomarkers up to a scan number of 280 (1 hour total incubation time per 96 well plate). While in some cases, such as in FIG. 5, no overall benefit to increasing the scan number further may be realized, this may be different for certain extremely tightly bound biomarkers and for metabolites as outlined in Example 5.

Figure 6:
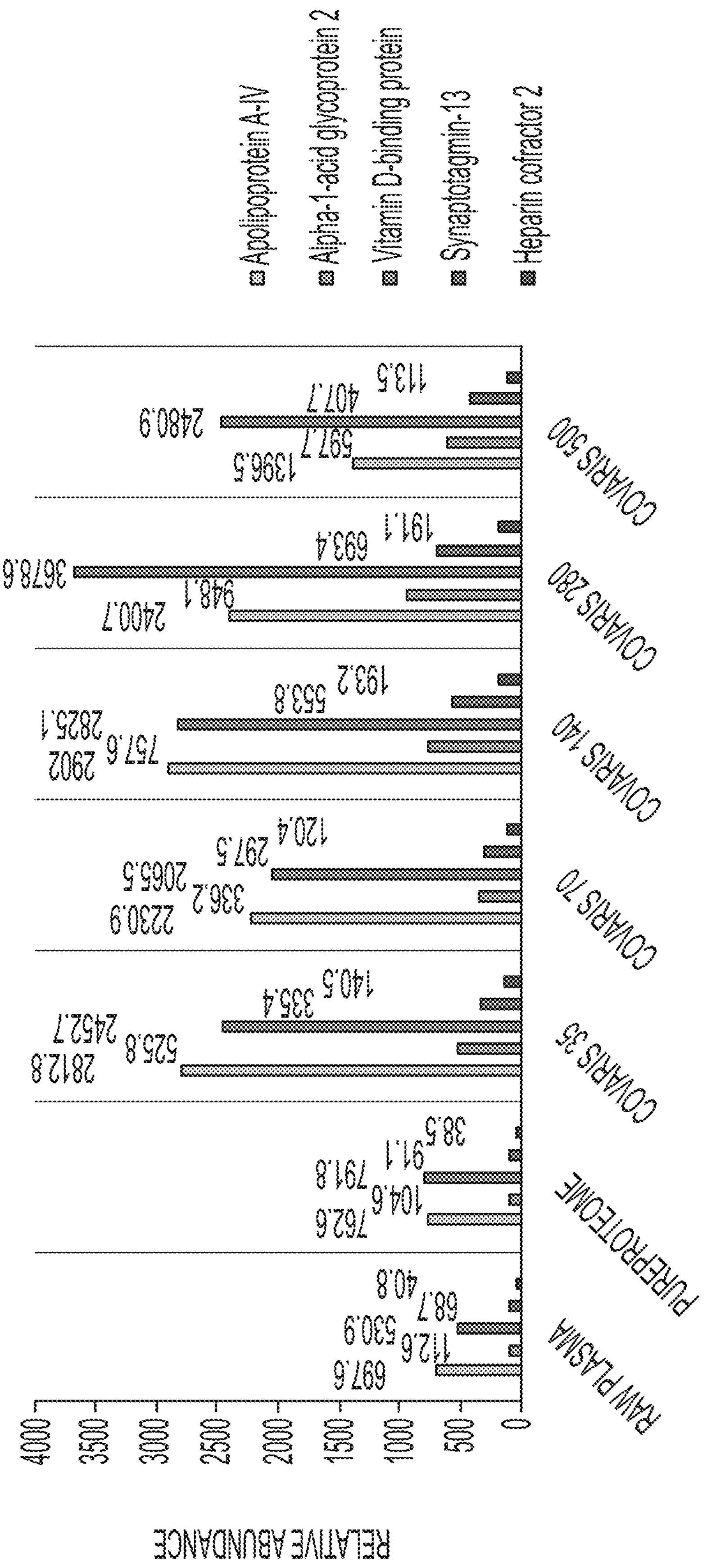
FIG. 6 illustrates the relative abundance of selected biomarkers or low abundance proteins in raw plasma, and plasma processed using the commercial depletion kit of FIG. 3 without acoustic energy and with acoustic energy.

FIG. 6 shows that for certain protein biomarkers, focused acoustic energy treatment can enhance the recovery of biomarkers during high-abundance protein binding compared to a passive mixing process that does not employ focused acoustic energy. This is especially important when using non-denaturing buffers (as required for most affinity based binding matrices or depletion media) and ambient temperature during the process. FIG. 6 shows the relative abundance of five selected biomarkers for each of the sample types in the example above, e.g., "Covaris 35" corresponds to 35 scans, and so on. All of the selected biomarkers have a higher relative abundance for the focused acoustic energy treated samples than the sample subjected to depletion without focused acoustic energy. Here nano and micro-streaming of bubbles as induced by focused acoustic energy are believed to break the non-covalent inter-molecule binding between proteins and thereby disassociate targeted proteins from other compounds.

A further analysis of total proteins identified in plasma that was treated with focused acoustic energy during albumin and immunoglobulin depletion produced larger numbers of identifiable peptides and protein groups since

TABLE 3

| | Fold Increase as Compared to Raw Plasma (LC-MS) | | | | | |
|---|---|---|---|---|---|---|
| Plasma Protein Biomarker | Pure Proteome | AFA 35 | AFA 70 | AFA 140 | AFA 280 | AFA 500 |
| Expected Enrichment Factor (Albumin/immunoglobulin in enriched/raw plasma) | 5.4 | 2.4 | 2.8 | 3.9 | 3.7 | 4.9 |
| Apoliprotein A-II | 2.5 | 7.7 | 5.6 | 5.5 | 5.6 | 2.9 |
| Pigment epithelium-derived Factor | 1.9 | 3.8 | 3.8 | 3.8 | 4.7 | 3.1 |
| Zinc-alpha-2-glycoprotein | 1.5 | 3.9 | 3.6 | 3:7 | 5.2 | 4.9 |
| Beta-2-glycoprotein 1 | 1.3 | 4.4 | 3.3 | 2.6 | 2.6 | 1.9 |
| inter-alpha-trypsin inhibitor HeavyChain H2 | 1.3 | 3.7 | 3.5 | 3.5 | 29 | 2.2 |
| isoforrn 2 of Gelsolin | 1.3 | 4.8 | 4.0 | 4.4 | 6.1 | 4.0 |
| Clusterin | 0.5 | 2.1 | 1.4 | 2.1 | 1.9 | 1.2 |
| kastatin | 0.9 | 3.4 | 2.5 | 3.4 | 3.3 | 1.6 |
| APOC4-APOC2 readthrough | 1.0 | 3.2 | 2.7 | 3.5 | 2.3 | 1.3 |
| Thyroxine-binding globulin | 1.4 | 5.1 | 3.4 | 4.6 | 7.0 | 5.6 |
| Serum amyioid P-component | 1.8 | 4.1 | 3.3 | 3.9 | 4.1 | 2.1 |
| Keratin,type II cytoskeletal | 1.1 | 1.3 | 5.2 | 10.4 | 11.3 | 2.4 |
| Apolipoprotein A-V | 1.1 | 4.0 | 3.2 | 4.2 | 3.4 | 2.0 |
| Alpha-1-acid glycoprotein 2 | 0.9 | 4.7 | 3.0 | 6.7 | 8.4 | 5.3 |
| Vitamin D-bincling protein | 1.5 | 4.6 | 3.9 | 5.3 | 6.9 | 4.7 |
| Synaptotagmin43 | 1.3 | 4.9 | 4.3 | 8.0 | 10.0 | 5.9 |
| Heparin cofactor 2 | 1.0 | 3.4 | 2.9 | 4.7 | 4.7 | 2.8 |

Figure 5:
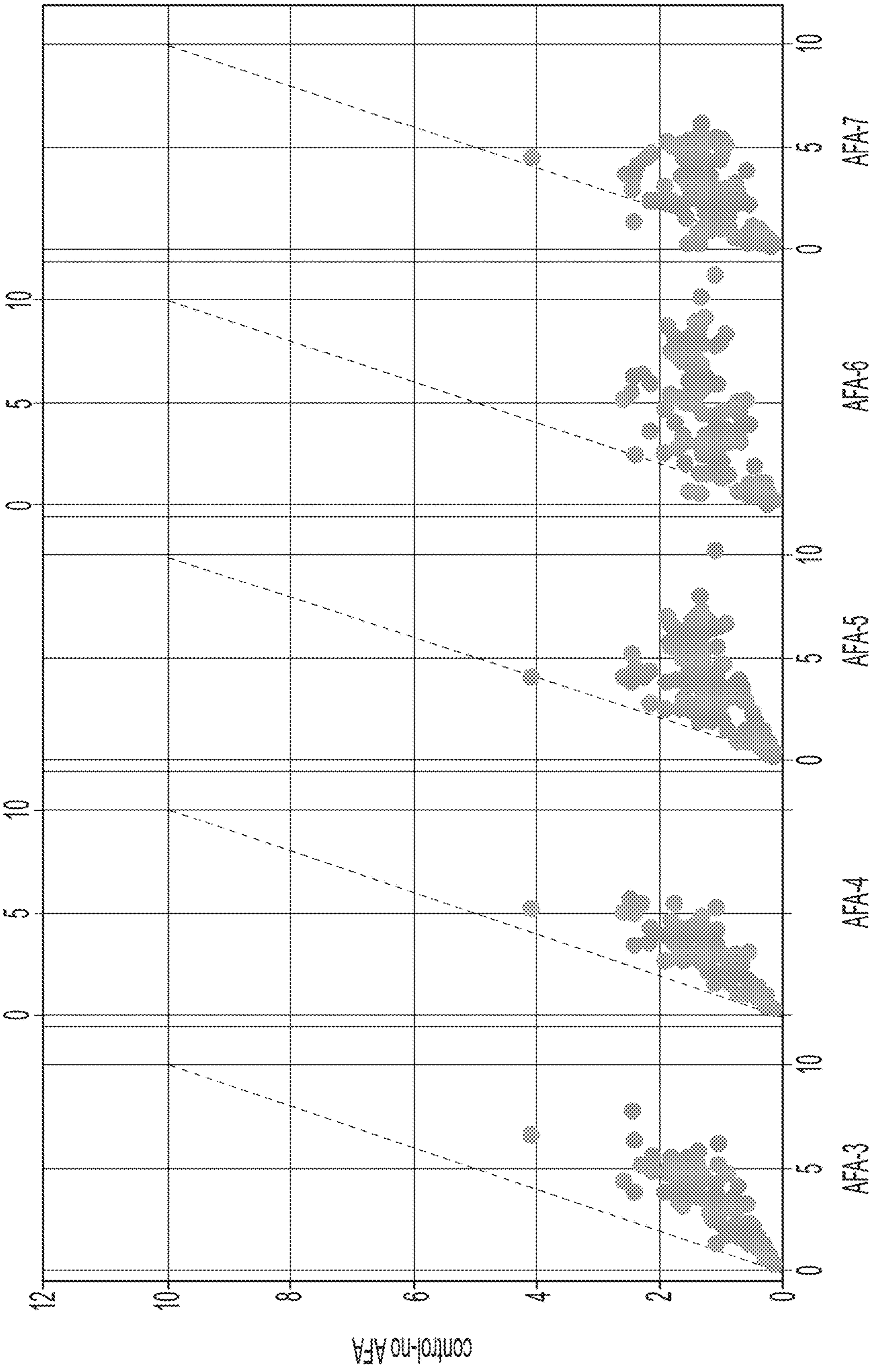
FIG. 5 illustrates a plot of focused acoustic energy treated samples as a function of samples processed according to the commercial depletion kit of FIG. 3 not treated with focused acoustic energy.
Figure 7:
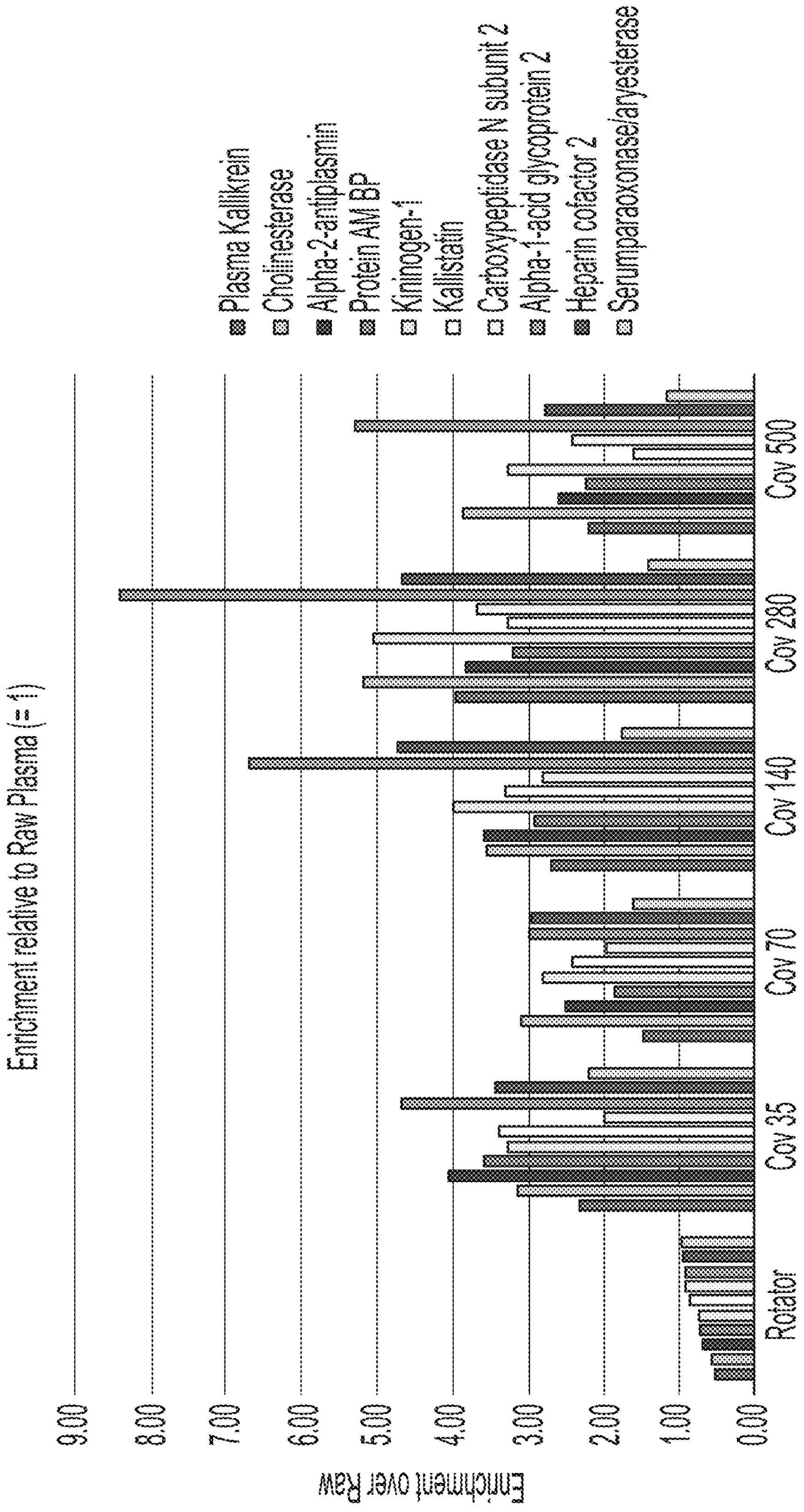
FIG. 7 shows example biomarkers or proteins that were enriched so as to be actually recoverable in the focused acoustic energy treated samples of FIG. 3 as compared to samples processed according to the commercial depletion kit of FIG. 3 without acoustic energy treatment.

The level of enrichment of protein biomarkers and/or low abundance proteins has been found to be dependent on focused acoustic energy as can be seen in FIG. 5. In FIG. 5, the abundance of all proteins in the focused acoustic energy-treated samples as detected in the LC-MS analysis is compared against the abundance of all proteins in the PureProteome kit (Manufacturer's protocol—with no focused acoustic energy) samples. (In FIG. 5, AFA-3 corresponds to 35 scans, AFA-4 corresponds to 70 scans, AFA-5 corresponds to 140 scans, AFA-6 corresponds to 280 scans, and AFA-7 corresponds to 500 scans.) Increasing the total energy (number of focused acoustic energy scans) applied to the samples resulted in increased enrichment of protein focused acoustic energy enabled better dissociation of proteins and peptides from high abundance proteins (especially albumin) which are otherwise removed during the affinity-depletion step. For example, FIG. 7 shows biomarkers (proteins) that were enriched such that the biomarkers were recoverable and/or identifiable to a greater extent in FIG. 3 type samples that were treated with focused acoustic energy compared to samples in raw serum and those processed using the PureProteome kit (Manufacturer's protocol—Rotator) without focused acoustic energy. In fact, the proteins shown in FIG. 7 were reduced in abundance by the PureProteome kit without acoustic energy treatment as compared to the raw serum. In other words, compared to the proteins in raw serum, the PureProteome kit actually reduced the abundance of selected proteins by co-depletion of the biomarker proteins with the higher abundance proteins. It is known that several low abundance proteins that are co-depleted by conventional protein depletion kits can bear high importance owing to their specific functionality and are important for research and/or diagnosis. For example, Plasma Kallikrein is a bradykinin-producing enzyme. Liver-derived prekallikrein is bound to high molecular weight kininogen and is converted to active kallikrein by Factor XII. This protein is associated with thrombosis and vascular inflammation in a host of diseases.

(High Molecular weight) Kininogen: A precursor protein of the kallikrein-kinin complex has two serine proteases, prekallikrein (pKal) and factor XII (FXII), and a cofactor, which is high-molecular-weight kininogen (HK). Upon activation of the KKS, HK is cleaved to release bradykinin. This protein has been found to play an important role in autoimmune disease progression and inflammation biomarker.

Protein AMBP: Precursor of alpha-1-microglubulin, inter-alpha-trypsin inhibitor and Trypstatin. Products inhibit trypsin, plasmin and lysosomal granulocytic elastase. This protein has been found to be an inflammation biomarker.

Example Five: Quantitation of Protein-Protein or Metabolites-Protein Affinity and Increased Sensitivity Detection of Biomarkers from Plasma Metabolites and their concentrations are essential for understanding biochemical functionalities and the domain of metabolomics have found widespread use in many areas of biomarker research: a few examples include action and toxicology of drugs and characterization of cancer cell metabolism. In cellular systems, detailed quantitative metabolomics data are required for both intra- and extra-cellular compartment. In recent years, several targeted metabolomics approaches have been developed using LC-MS and NMR methods.

For studies involving protein-metabolites interaction in plasma, Human Serum Albumin (HSA) is the most abundant plasma protein (about 60% of all plasma protein) and it drives the transport of endogenous (fatty acids) and exogenous metabolites (e.g., drugs). HSA has multiple binding sites and is highly flexible. Several different saturated and non-saturated fatty acids bind to HSA and the binding sites provide accommodation of several endogenous and exogenous ligands, which include a broad variety of drugs, such as, ibuprofen, propofol, and warfarin. Under physiological conditions, HSA binds not only endogenous and exogenous low molecular weight compounds, but also peptides and proteins.

To obtain correct measured metabolic profiles of blood plasma and/or for information on HSA and fatty acids content, it is necessary to quantify both endogenous and exogeneous metabolite-protein interactions. Metabolite-protein interaction can be either strong or weak as detected by liquid 1H-NMR. Both NMR and mass spectrometry techniques can detect and quantify either free or protein conjugated metabolite concentration in plasma, however, developing comprehensive knowledge of the strength of the protein-metabolite complex can be challenging and typically involves time consuming experiments that relies on passive diffusion. Typically, exact metabolite concentration can be determined for the non-interacting metabolites but the interacting metabolite concentration can only be estimated. In addition, the strength of interacting metabolites could be used as a biomarker in drug discovery, diagnostic studies, or trauma or cardiovascular diseases.

The use of focused acoustic energy by treating plasma samples enables a dose response of protein-protein and/or metabolite-protein interaction strength that can be monitored and quantified using NMR/LC-MS. This ability to monitor dose response is achieved by adjusting the Average Incident Power courses of the focused acoustic energy during treatment. As described above, different levels of total focused acoustic energy applied to a sample will disassociate protein complexes to varying extents. In addition, focused acoustic energy enables the dissociation of biomolecules bound to HSA and enhances quantitation method sensitivity to biomarkers, which might be lost when HSA plasma depletion is performed.

Example Six: Multiplex Immunoassays

In this example, the effects of focused acoustic energy in separating low abundance proteins from Human Serum Albumin (HSA) and other highly abundant proteins (such as immunoglobulins) is explored. Several antibody-, aptamer- or aggregation-based technologies would benefit from a better homogenization of plasma or serum, leading to an even distribution of low abundance proteins.

Multiplexed immunoassays include, but are not restricted to, technologies from the following companies: Luminex, Meso Scale Discovery, Ray Biotech, Olink, nPLEX, RPPA.

Multiplexed Aptamer-based assays include, but not restricted to: SomaLogic SOMAscan, ELAA.

Aggregation capture assays include, but are not restricted to: Seer Proteograph.

The process is as follows:

1. Procure Human plasma samples (not pooled).
2. Dilute as appropriate for a final volume in accordance with the manufacturer's technology, ideally in 5 to 15 microliter volume range.
3. Treat the samples with focused acoustic energy for disassociation of protein complexes; other samples are not treated and are control samples. Each patient sample should be split and used for treated and control samples (biological samples), in triplicates (technical replicates).
4. Process the samples in accordance with manufacturer's technology—likely an incubation step with the capture or binding element followed by one or more washing steps.
5. Carry out the assay on the appropriate analysis equipment.
6. Calculate data for amount of each individual protein target, and compare for each replicate of each sample, focused acoustic energy treated vs untreated.
7. Calculate reproducibility and Z'.

The focused acoustic energy treated samples are expected to have a similar or greater amount of each protein compared to the untreated samples. Also, an improved CV and an improved Z1 with focused acoustic energy treated samples should be found as compared to the control samples.

Figure 8:
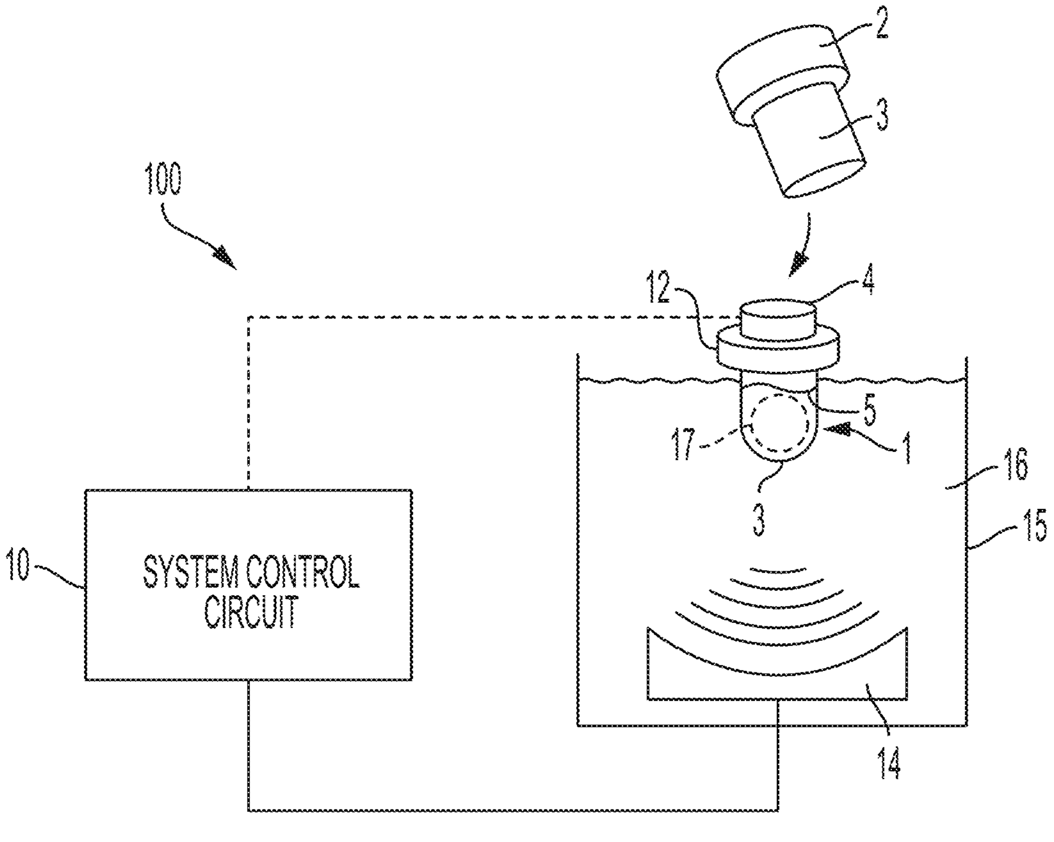
FIG. 8 is a schematic diagram of a sample processing system in an illustrative embodiment.

FIG. 8 shows a schematic block diagram of an acoustic treatment system 100 that incorporates one or more aspects of the present disclosure and/or can be employed with one or more aspects of the invention described herein. It should be understood that although embodiments described herein may include most or all aspects of the invention(s), aspects of the invention(s) may be used alone or in any suitable combination with other aspects of the invention(s).

In this illustrative embodiment, the acoustic treatment system 100 includes an acoustic energy source with an acoustic transducer 14 (e.g., including one or more piezoelectric elements) that is capable of generating an acoustic field (e.g., at a focal zone 17) suitable to cause mixing, e.g., caused by cavitation, and/or other affects on a sample contained in a vessel 4. The sample may include solid particles and/or liquid material in the vessel. Acoustic energy may be transmitted from the transducer 14 to the vessel 4 through a coupling medium 16, such as a liquid (e.g., water), a gel or other semi-solid, or a solid, such as a silica, metal or other material. Thus, the transducer 14 is spaced from the vessel 4 and can transmit acoustic energy from outside the vessel volume for transmission into the vessel 4 via the coupling medium 16. Where the coupling medium 16 is a liquid, a coupling medium container 15 may be used to hold the coupling medium 16.

The vessel 4 may have any suitable size or other arrangement, e.g., may be a glass or metal tube, a plastic container, a well in a microtiter plate, a vial, or other, and may be supported at a location by a vessel holder 12. Although a vessel holder 12 is not necessarily required, the vessel holder 12 may interface with the control circuit 10 so that the vessel 4 and the sample in the vessel is positioned in a known location relative to an acoustic field, for example, at least partially within a focal zone 17 of acoustic energy. In this embodiment, the vessel 4 is a 130 microliter borosilicate glass tube, but it should be understood that the vessel 4 may have other suitable shapes, sizes, materials, or other feature, as discussed more below. For example, the vessel 4 may be a cylindrical tube with a flat bottom and a threaded top end to receive a cap 2, may include a cylindrical collar with a depending flexible bag-like portion to hold a sample, may be a single well in a multiwell plate, may be a cube-shaped vessel, or may be of any other suitable arrangement. The vessel 4 may be formed of glass, plastic, metal, composites, and/or any suitable combinations of materials, and formed by any suitable process, such as molding, machining, stamping, and/or a combination of processes.

The transducer 14 can be formed of a piezoelectric material, such as a piezoelectric ceramic. In some embodiments, the ceramic may be fabricated as a "dome," which tends to focus the energy. One application of such materials is in sound reproduction; however, as used herein, the frequency is generally much higher and the piezoelectric material would be typically overdriven, that is driven by a voltage beyond the linear region of mechanical response to voltage change, to sharpen the pulses. Typically, these domes have a longer focal length than that found in lithotriptic systems, for example, about 20 cm versus about 10 cm focal length. Ceramic domes can be damped to prevent ringing or undamped to increase power output. The response may be linear if not overdriven. The high-energy focus zone of one of these domes may be cigar-shaped. At 1 MHz, the focal zone is about 6 cm long and about 2 cm wide for a 20 cm dome, or about 15 mm long and about 3 mm wide for a 10 cm dome. The peak positive pressure obtained from such systems is about 1 MPa (mega Pascal) to about 10 MPa pressure, or about 150 PSI (pounds per square inch) to about 1500 PSI, depending on the driving voltage. The focal zone 17, defined as having an acoustic intensity within about 6 dB of the peak acoustic intensity, is formed around the geometric focal point. It is also possible to generate a line-shaped focal zone, e.g., that spans the width of a multi-well plate and enables the system 100 to treat multiple samples simultaneously. Other arrangements for producing focused acoustic energy are possible. For example, a flat transducer may be provided with a tapered waveguide for focusing or otherwise channeling acoustic energy emitted from the transducer toward a relatively small space where the sample and vessel are located.

To control an acoustic transducer 14, the acoustic treatment system 100 may include a system control circuit 10 that controls various functions of the system 100 including operation of the acoustic transducer 14. For example, the system control circuit 10 may provide control signals to a load current control circuit, which controls a load current in a winding of a transformer. Based on the load current, the transformer may output a drive signal to a matching network, which is coupled to the acoustic transducer 14 and provides suitable signals for the transducer 14 to produce desired acoustic energy. Moreover, the system control circuit 10 may control various other acoustic treatment system 100 functions, such as positioning of the vessel 4 and/or acoustic transducer 14, receiving operator input (such as commands for system operation), outputting information (e.g., to a visible display screen, indicator lights, sample treatment status information in electronic data form, and so on), and others. Thus, the system control circuit 10 may include any suitable components to perform desired control, communication and/or other functions. For example, the system control circuit 10 may include one or more general purpose computers, a network of computers, one or more microprocessors, etc. for performing data processing functions, one or more memories for storing data and/or operating instructions (e.g., including volatile and/or non-volatile memories such as optical disks and disk drives, semiconductor memory, magnetic tape or disk memories, and so on), communication buses or other communication devices for wired or wireless communication (e.g., including various wires, switches, connectors, Ethernet communication devices, WLAN communication devices, and so on), software or other computer-executable instructions (e.g., including instructions for carrying out functions related to controlling the load current control circuit as described above and other components), a power supply or other power source (such as a plug for mating with an electrical outlet, batteries, transformers, etc.), relays and/or other switching devices, mechanical linkages, one or more sensors or data input devices (such as a sensor to detect a temperature and/or presence of the medium 16, a video camera or other imaging device to capture and analyze image information regarding the vessel 4 or other components, position sensors to indicate positions of the acoustic transducer 14 and/or the vessel 4, and so on), user data input devices (such as buttons, dials, knobs, a keyboard, a touch screen or other), information display devices (such as an LCD display, indicator lights, a printer, etc.), and/or other components for providing desired input/output and control functions.

Under the control of a control circuit 10, the acoustic transducer 14 may produce acoustic energy within a frequency range of between about 100 kilohertz and about 100 megahertz such that the focal zone 17 has a width of about 2 centimeters or less. The focal zone 17 of the acoustic energy may be any suitable shape, such as spherical, ellipsoidal, rod-shaped, or column-shaped, for example, and be positioned at the sample. The focal zone 17 may be larger than the sample volume, or may be smaller than the sample volume, as shown in FIG. 3. U.S. Pat. Nos. 6,948,843 and 6,719,449 are incorporated by reference herein for details regarding the construction and operation of an acoustic transducer and its control.

In an embodiment where the acoustic treatment system 100 is a Covaris device, acoustic treatment may be applied using a duty cycle, a peak incident power (PIP), cycles per burst (CPB), for a suitable period of time as discussed above. Of course, other duty cycles, peak power, cycles per burst and/or time periods may be used to produce a sufficient amount of power for processing different samples. For example, to achieve desirable results with regard to extraction and recovery of biomolecules from a sample and with regard to quality of the extracted biomolecules, the acoustic transducer may be operated at a peak intensity power of between 10 W and 500 W, a duty factor of between 10% and 90% and a cycles per burst of between 100 and 1000, for an appropriate duration of time. It can be appreciated that the acoustic transducer may be operated so as to produce focused acoustic energy that results in a suitable level of energy input to the sample material.

In some embodiments, the transducer may generate acoustic energy having a peak incident power over the course of a period of time that produces a particular amount of energy, to achieve preferred results. As described herein, the peak incident power (PIP) is the power emitted from the transducer during the active period of one cycle. The peak incident power, in some cases, may control the amplitude of the acoustic oscillations. The energy applied to the sample material may be determined from the peak incident power of the applied acoustic energy and the duration of the acoustic treatment period. In some embodiments, to suitably lyse cells and extract or otherwise operate on the target biomolecule(s) from a sample, the acoustic transducer may be operated so as to generate focused acoustic energy according to a peak incident power of greater than or equal to 10 Watts, e.g., up to 500 Watts.

The acoustic transducer may be operated at a suitable duty factor, in combination with other parameters, to generate focused acoustic energy that leads to preferred results. As described herein, the duty factor is the percentage of time in a cycle in which the transducer is actively emitting acoustic energy. For example, a duty factor of 60% refers to the transducer being operated in an "on" state 60% of the time, and in an "off" state 40% of the time. In some embodiments, in appropriately lysing cells and extracting/processing the target biomolecule(s) from a sample, the acoustic transducer may be operated at a duty factor setting of greater than or equal to 10%, greater than or equal to 20%, greater than or equal to 30%, greater than or equal to 40%, greater than or equal to 50%, greater than or equal to 60%, greater than or equal to 70%, or greater than or equal to 80%, or other values outside of these ranges.

The acoustic transducer may be operated according to a suitable cycles-per-burst setting to achieve preferred results. As described herein, the cycles per burst (CPB) is the number of acoustic oscillations contained in the active period of one cycle. In some embodiments, to lyse and extract/process the target biomolecule(s) from a sample, the acoustic transducer may be operated to generate focused acoustic energy according to a cycles per burst setting of greater than or equal to 50, greater than or equal to 100, greater than or equal to 150, greater than or equal to 200, or other values outside of these ranges.

Although not necessarily critical to employing aspects of the invention, in some embodiments, sample treatment control may include a feedback loop for regulating at least one of acoustic energy location, frequency, pattern, intensity, duration, and/or absorbed dose of the acoustic energy to achieve the desired result of acoustic treatment. One or more sensors may be employed by the control circuit to sense parameters of the acoustic energy emitted by the transducer and/or of the mixture, and the control circuit may adjust parameters of the acoustic energy and/or of the mixture (such as flow rate, concentration, etc.) accordingly. Thus, control of the acoustic energy source may be performed by a system control unit using a feedback control mechanism so that any of accuracy, reproducibility, speed of processing, control of temperature, provision of uniformity of exposure to sonic pulses, sensing of degree of completion of processing, monitoring of cavitation, and control of beam properties (including intensity, frequency, degree of focusing, wave train pattern, and position), can enhance performance of the treatment system. A variety of sensors or sensed properties may be used by the control circuit for providing input for feedback control. These properties can include sensing of temperature, cell concentration or other characteristic of the mixture; sonic beam intensity; pressure; coupling medium properties including temperature, salinity, and polarity; chamber position; conductivity, impedance, inductance, and/or the magnetic equivalents of these properties, and optical or visual properties of the mixture. These optical properties, which may be detected by a sensor typically in the visible, IR, and UV ranges, may include apparent color, emission, absorption, fluorescence, phosphorescence, scattering, particle size, laser/Doppler fluid and particle velocities, and effective viscosity. Mixture integrity and/or comminution can be sensed with a pattern analysis of an optical signal from the sensor. Particle size, solubility level, physical uniformity and the form of particles could all be measured using instrumentation either fully standalone sampling of the fluid and providing a feedback signal, or integrated directly with the focused acoustical system via measurement interface points such as an optical window. Any sensed property or combination thereof can serve as input into a control system. The feedback can be used to control any output of the system, for example beam properties, flow in the chamber, treatment duration, and losses of energy at boundaries and in transit via reflection, dispersion, diffraction, absorption, dephasing and detuning.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

The use of "including," "comprising," "having," "containing," "involving," and/or variations thereof herein, is meant to encompass the items listed thereafter and equivalents thereof as well as additional items.

It should also be understood that, unless clearly indicated to the contrary, in any methods claimed herein that include more than one step or act, the order of the steps or acts of the method is not necessarily limited to the order in which the steps or acts of the method are recited.

While aspects of the present disclosure have been described with reference to various illustrative embodiments, such aspects are not limited to the embodiments described. Thus, it is evident that many alternatives, modifications, and variations of the embodiments described will be apparent to those skilled in the art. Accordingly, embodiments as set forth herein are intended to be illustrative, not limiting. Various changes may be made without departing from the spirit of aspects of the present disclosure.

The invention claimed is:

1. A method of analyzing proteins in a sample, comprising:

Providing a sample including a plurality of different types of protein, at least two of the types of protein forming a plurality of complexes in which a first protein is bound to a second protein;

Exposing the sample to focused acoustic energy to disrupt the plurality of complexes and disassociate the first protein from the second protein in each of the complexes, wherein the focused acoustic energy has a peak incident power (PIP) between 10 to 500 W, a duty factor between 10% and 90%, and cycles per burst between 100 to 1000;

Disassociating the first protein from the second protein in each of the complexes such that the first protein is separated from the second protein; and Recovering the first protein from the sample after disassociating the first protein from the second protein.

2. The method of claim 1, wherein the second protein has a higher molecular weight than the first protein.

3. The method of claim 1, wherein the first protein is sequestered at least partially within the second protein prior to disassociation from the second protein.

4. The method of claim 1, wherein the disassociation of the first and second proteins is achieved at a sample temperature below 60 degrees C.

5. The method of claim 1, further comprising depleting the sample of the second protein.

6. The method of claim 5, further comprising identifying the first protein from the sample after depletion of the second protein from the sample.

7. The method of claim 1, wherein the sample includes blood plasma, and the first protein is present in the sample at a first concentration that is at least an order of magnitude lower than a second concentration at which the second protein is present in the sample.

8. The method of claim 7, wherein the first protein is present in the sample free of any complex with the first protein.

9. The method of claim 1, wherein types of proteins other than the first and second types of proteins are present in the sample.

10. The method of claim 1, wherein disassociation of the first and second proteins from the complexes by exposing the sample to focused acoustic energy increases a measurable concentration of the first protein in the sample.

11. The method of claim 1, wherein the disassociation of the first and second proteins is achieved without use of a solvent effective to perform the disassociation or with use of a non-denaturing buffer.

12. The method of claim 1, wherein the step of exposing the sample to focused acoustic energy is performed while the sample includes a protein depletion medium configured to bind to proteins targeted for depletion from the sample.

13. The method of claim 12, wherein the protein depletion medium includes magnetic beads.

14. The method of claim 12, wherein the proteins targeted for depletion include albumin and immunoglobulin.

15. The method of claim 1, wherein the first protein includes Alpha-1-acid glycoprotein, synaptotagmin-13 or Heparin cofactor-2.

16. The method of claim 1, wherein the step of exposing the sample to focused acoustic energy includes adjusting a total amount of acoustic energy applied to the sample to adjust a level or rate of disassociation of selected ones of the plurality of complexes.

17. The method of claim 1, further comprising analyzing the first protein after disassociating the first protein from the second protein.

18. A method of analyzing proteins and/or metabolites in a sample, comprising:

Providing a sample including at least one protein and a metabolite, the at least one protein and the metabolite forming a plurality of complexes in which the metabolite is bound to a protein;

Exposing the sample to focused acoustic energy to disrupt the plurality of complexes and disassociate the metabolite from the protein of each of the complexes, wherein the focused acoustic energy has a peak incident power (PIP) between 10 to 500 W, a duty factor between 10% to 90%, and cycles per burst between 100 to 1000;

Disassociating the metabolite from the protein in each of the complexes such that the metabolite is separated from the protein; and Recovering the metabolite or the protein from the sample after disassociating the metabolite from the protein.

19. The method of claim 18, wherein the protein has a higher molecular weight than the metabolite.

20. The method of claim 18, wherein the metabolite is sequestered at least partially within the protein prior to disassociation of the metabolite from the protein.

21. The method of claim 18, wherein the disassociation of the plurality of complexes is achieved at a sample temperature below 60 degrees C.

22. The method of claim 18, further comprising depleting the sample of the protein.

23. The method of claim 22, wherein the step of recovering the metabolite from the sample occurs after depletion of the protein from the sample.

24. The method of claim 18, wherein the sample includes blood plasma, and the metabolite is present in the sample at a first concentration that is at least an order of magnitude lower than a second concentration at which the protein is present in the sample.

25. The method of claim 24, wherein the metabolite is present in the sample free of any complex with the protein.

26. The method of claim 18, wherein disassociation of the plurality of complexes by exposing the sample to focused acoustic energy increases a measurable concentration of the metabolite in the sample.

27. The method of claim 18, further comprising analyzing the metabolite or the protein after disassociating the metabolite from the protein.

* * * * *